United States Patent [19]

Tomasini

[11] Patent Number: 4,738,620
[45] Date of Patent: Apr. 19, 1988

[54] DENTAL APPARATUS FOR TOOTH REAMING AND PROCESS

[76] Inventor: Gianni Tomasini, Via Col di Lana, 6 - 20100 Milan, Italy

[21] Appl. No.: 869,971

[22] Filed: Jun. 2, 1986

[30] Foreign Application Priority Data

Jun. 6, 1985 [IT] Italy ................................ 21062 A/85

[51] Int. Cl.⁴ .............................................. A61C 19/04
[52] U.S. Cl. ........................................ 433/72; 433/224
[58] Field of Search ......................... 433/102, 72, 224; 604/117

[56] References Cited

U.S. PATENT DOCUMENTS

| | | | |
|---|---|---|---|
| 2,901,826 | 9/1959 | Kline et al. | 433/165 |
| 3,358,826 | 12/1967 | Siegel | 433/102 |
| 3,483,810 | 12/1969 | Peters et al. | 604/117 |
| 3,781,996 | 1/1974 | Saffro | 433/75 |
| 3,855,705 | 12/1974 | Malmin | 423/32 |

*Primary Examiner*—Robert Peshock
*Attorney, Agent, or Firm*—Young & Thompson

[57] ABSTRACT

The new apparatus for tooth reaming by a flexible reamer, for devitalization of the tooth, comprises a front cutter (10) to establish a reference surface in the tooth, a detector (22) to measure the tooth by using the reference surface, and substantially rigid adaptors (24, 124) to be applied on the reamer (30) to make it fit to the detected measurement.

2 Claims, 2 Drawing Sheets

U.S. Patent   Apr. 19, 1988   Sheet 1 of 2   4,738,620
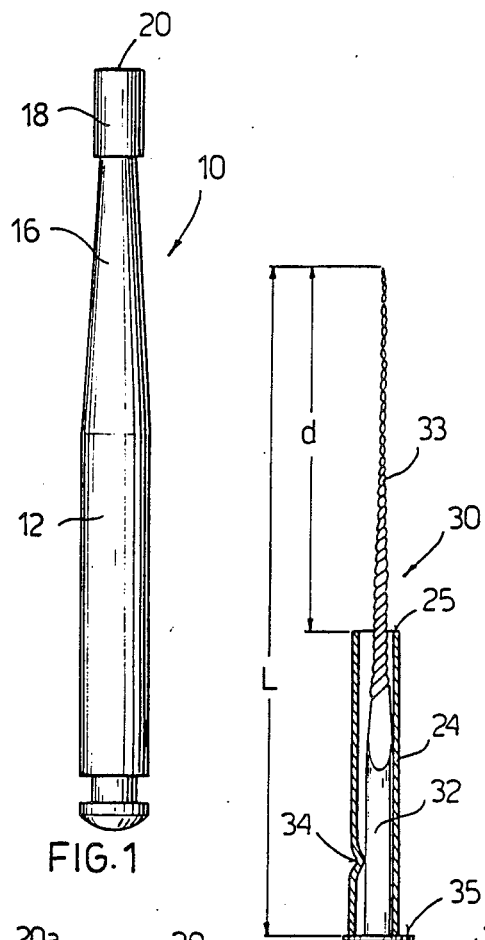
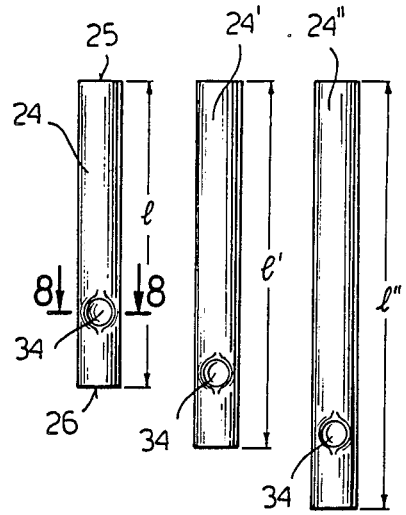
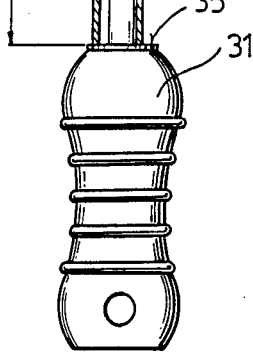
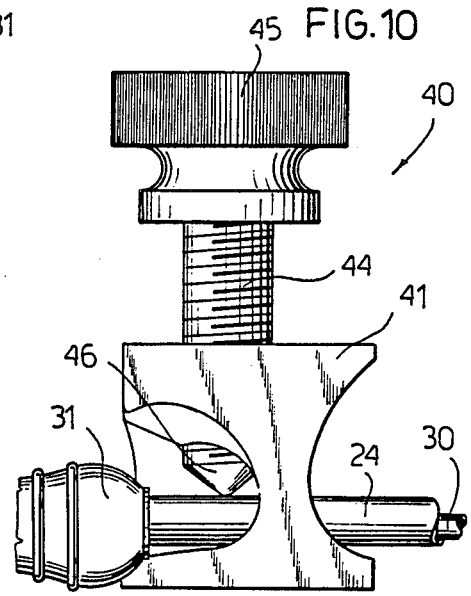

DENTAL APPARATUS FOR TOOTH REAMING AND PROCESS

FILED OF THE INVENTION

The present application refers to the field of dental apparatus or equipment for operative dentistry.

BACKGROUND OF THE INVENTION

A frequent problem in dentistry is the devitalization of a tooth, that is the removal of the dental pulp from the pulp chamber or cavity. This is generally carried out by means of flexible thin reamers. These reamers comprise a handle and a flexible blade with helicoidal cutting edge and are used by rotating them manually or by motor; their flexibility allows them fit to pulp chambers of different curving. Generally a series of reamers or files of increasing diameter are used to empty the pulp chamber. A risk present in this way of proceeding is that the operator does not have an exact perception of the point in the cavity reached by the tip of the reamer; thus it can happen that the emptying of the pulp chamber is incomplete or the tooth apex is pierced, and in both cases a clinically valid methodology for a good devitalization is not followed.

DESCRIPTION OF THE PRIOR ART

To obviate in part to said drawbacks a removable stop in the form of a ring, in rubber or similar, is applied on a tang part of the reamer; the rubber ring is fixed to a distance from the tip of the reamer established according to the finding of the tooth x-ray or radiograph. The results thus obtained, however, are not satisfactory, both because the rubber ring sets on a tooth surface which is at times decayed or chipped, unsuitable then to determine a precise position and because the ring itself is flexible and does not make for a reliable stop.

An aim of this invention is to give the possibility of carrying out the reaming of the tooth pulp cavity with precision down to the desired depth.

SUMMARY OF THE INVENTION

The aim has been achieved with an apparatus or equipment or kit comprising a series of tubular shaped adaptors or tubes, made of a substantially rigid material, of various lengths, having sufficient internal dimension to be placed around the reamer and slide on it, and with opposite abutment surfaces. Each adaptor has one or more retaining means, generally in the form of internal projections, so that, when the adaptor is mounted on the reamer it comes into contact with the latter with the tip of the projection/s; this is sufficient, in the absence of applied force, to keep the tube integral with the reamer.

The apparatus preferably comprises also a mill or cutter having a front cutting face, a radiopaque element visible under radiography, a measuring device, and a puching device to carry out or rectify a punching on the adaptors.

The cutter diameter is preferably slightly bigger than the tubes external diameter.

Preferably, the adaptors have a marking corresponding to the type of reamer to which they have to be fitted and a marking regarding their length; these markings are generally different colours.

To devitalize a tooth, the following steps are taken in succession. Once the tooth has been cleaned internally, by means of the front cutter a reference surface, generally at the bottom of a hole, is carried out; the radiopaque means is then placed inside the hole, against the reference surface and a tooth X-ray is taken.

On it, preferably by means of the measuring device, a measurement relative to the position of the tooth apex is taken, for instance the distance between the tooth apex and the reference surface. It is then chosen an adaptor tube of suitable length to have the desired free length in the reamer and the adaptor is slipped onto the reamer until an abutment thereof comes to lay against an abutment of the reamer handle.

The reamer with the adaptor is inserted in the tooth till the adaptor's abutment surface, opposite to the one against the reamer handle, abuts on the reference surface of the tooth; the emptying of the pulp chamber is thus carried out precisely down to the measured depth.

The apparatus allows thus to avoid with certainty the risk of only partially emptying the pulp chamber and of piercing the apex.

BRIEF DESCRIPTION OF THE DRAWING

The invention is described in the following with reference to the enclosed drawings wherein:

FIG. 1 is a side view of a front cutter of the apparatus, on an enlarged scale;

FIG. 2 is a top plan view of FIG. 1;

FIG. 3 is a side view of a radiopague element for radiography, on an enlarged scale;

FIG. 4 is a top plan view of FIG. 3;

FIGS. 5, 6, 7 are side views of adaptor tubes, of various size, on an enlarged scale;

FIG. 8 is a sectional view according to 8—8 in FIG. 5;

FIG. 9 is a side view, on an enlarged scale, of a per se known flexible reamer, and shows an adaptor tube, drawn in an axial sectional view, applied thereon;

FIG. 10 shows, in side view, on an enlarged scale, a punching device; a tube to be punched is shown partially inserted in it; a tang of the reamer is inserted in the tube;

DESCRIPTION OF THE PREFERRED EMBODIMENTS

Figure 10A:
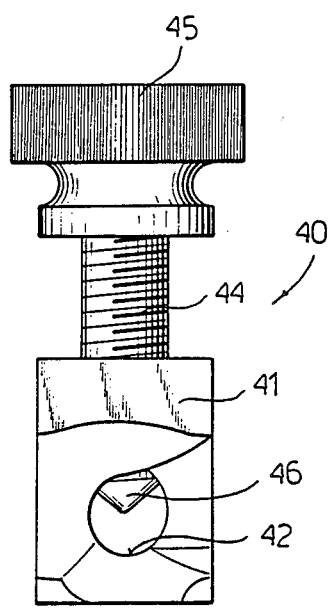
FIG. 10a is a front view of the punching device.

A devitalization apparatus, according to an embodiment, comprises a cutter or mill 10 having a front cutting surface. Cutter 10 comprises, in a per se known manner, a tang 12 for connection to a power drive; it comprises then a stem 16 and a head 18. Head 18 has a diamond front surface 20 or in any other way made cutting, except possibly for a crown surface 20a.

A radiopaque element 22 has preferably a cylindrical form, possibly tubular, is made of radiopaque material and is of any required length (preferably about 8 mm). The apparatus comprises in addition adaptors 24, 124 in tube form, of various length (FIGS. 5, 6, 7, 11) in a relatively rigid material. Said tubes have an internal dimater sufficient to receive a blade and a tang of a reamer 30, generally of the per se known type, shown in FIG. 9. The reamer 30 comprises a handle 31, a stem or tank 32, an abutment surface 35 and a flexible blade 33 with a helicoidal cutting edge. Although the shown reamer is of a manual type, the use of motor driven reamers is possible. The adaptors are appliable also to flexible files, although in the following, to make the description easy, reference is made only to reamers.

Each of the adaptor tubes of FIGS. 5, 6, 7 is of a substantially cylindrical shape and is provided with at least a retaining internal projection 34, generally obtained by deforming the side wall of the tube and herewith also called punching; the punchings or projections can be more than one for each tube, preferably angularly equidistant. Each adaptor has two end abutment surfaces 25, 26 which are substantially orthogonal to the adaptor axis.

Between the retaining projection 34 and the adaptor opposite surface a passage is defined, passage which is of dimensions such as to tightly house the reamer stem 32 in case by making use of a certain resilience of the material.

The punching 34 can be obtained in any known manner. A tool to make it or to deepen it can be provided by the kit or equipment of this invention and is shown in FIGS. 10, 10a. The puching tool of FIGS. 10 and 10a is indicated by 40 and comprises a body 41 with a through hole or housing 42 to receive tube 24, and a threaded hole, orthogonal to the housing. In this latter a threaded stem 44 with knob 45 and with a point 46 at the opposite end of the knob is housed by screwing.

After having placed in housing 42 an adaptor 24 and a reamer with the blade fixed in it, by screwing stem 44 in the threaded hole a punching is obtained or deepened at the required depth in the side of tube 24.

Figure 12:
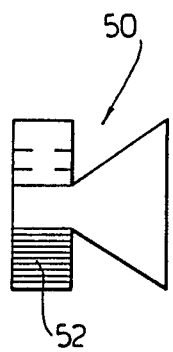
FIG. 12 shows a measuring element.

FIG. 12 shows a measuring element 50.

It has to be noted that, as reamers of different diameters are presently on the market, it will be advisable for the apparatus to comprise a series of tubes of various diameters. In each series, the tube will be of different length. To facilitate the choice of the tube, provision is made for it to have a colour indicating the diameter and a colour indicating the length. These colour indications can be applied directly on the external surface of each metallic tube 24; a preferred embodiment of tubes 124 of FIG. 11 comprises a plastic head 128 integral with a tubular metallic part 123. Head 128 is composed of two plastic parts 128′, 128″ of different colour. The adhesion to the reamer, in the case of adaptor 124, can be given by plastic burrs or fins 127 jutting from inside the plastic head.

The measuring element or implement 50, in its turn, besides a grading scale, or in the place of it, can have a scale 52 with a coloured graduation, the colours corresponding to the ones chosen to indicate the length of the tubes. Preferably the measuring implement is made of transparent material and on it a referring point (or more points) can be marked according to the length of the endodontic instruments available.

The kit can be equipped by means for sterilization of the components.

Figure 13:
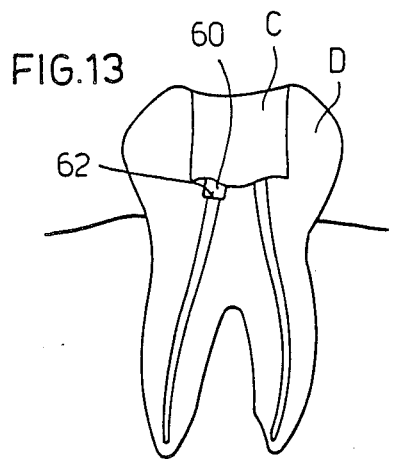
FIGS. 13, 14, 15 show various steps of the devitalization process of a tooth with the new apparatus.
Figure 14:
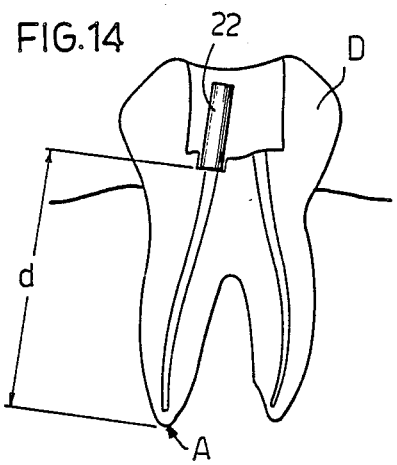
Figure 11:
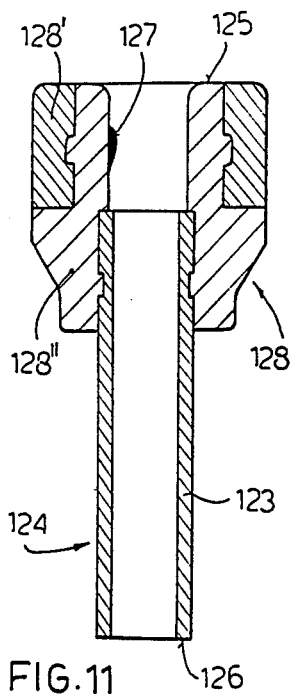
FIG. 11 shows in an enlarged axial sectional view, an actually preferred embodiment of an adaptor tube.
Figure 15:
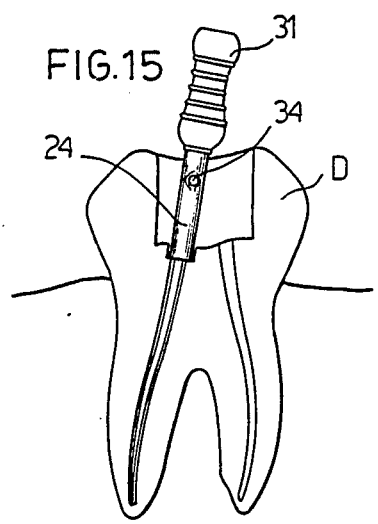

In FIGS. 13, 14 and 15 the devitalization process carried out with this application apparatus is shown.

Once the tooth D to be devitalized is cleaned internally thus obtaining the cavity C, a hole 60 is pierced in the proximity of the pulp channel and, by means of the front cutter 10, a flat referring surface 62 is obtained. The radiopaque cylindrical element 22 is introduced in the hole against the referring surface and an X-ray (or radiograph) is taken obtaining an image substantially corresponding to FIG. 14. On the radiograph by means of the measuring implement 50 a distance, e.g., d, between the tooth apical area A and the referring surface is measured, or another distance related to the apex position, using in case the colour code. A suitable reamer having for instance length L is chosen and an adaptor 24 or 124 of length 1 is also chosen, so that $L-1=d$. The tube is applied on the reamer, with surface 26 or 126 against abutment 35, and is retained on it in such a manner that it can slip away from it only by applying a certain axial force. The reamer with the tube fixed in it is introduced in the hole of the tooth and can be pushed inside it until the surface 25 or 125 of the adaptor is against the reference surface 62. This guarantees that the tip of the reamer does not pierce the tooth apex and that at the same time a through cleaning of the pulp cavity is carried out to the bottom. It has been noted that the adaptors, thanks to the punching, stay fairly firm on the reamer, without falling into the patient mouth; moreover, when the reamer is in the position of FIG. 15, it can be rotated easily without the tube being involved in the rotation.

What I claim is:

1. An apparatus for dental use to carry out the reaming of a root canal down to a desired depth by using a tool comprising an abutment and a thin flexible blade, said apparatus comprising interchangeable adaptors for the tool in the form of a series of tubes of various lengths, said adaptors having an abutment surface for abutting against said abutment of the tool and a further abutment surface for abutting on a reference surface established in the tooth, said tubes having gripping means detachably to keep them on the tool in the absence of any external force, in combination with a measuring element adapted to measure the length of a tooth root as shown on a radiograph, said element having differently colored areas indicating different lengths of tooth root, said adaptors each having a color indicating the length of the same, the colors of the adaptors of different length being shown on the measuring element.

2. A process to carry out the reaming of a root canal by means of a flexible blade tool, comprising the following steps: (a) etablishing a reference surface on the tooth by grinding at the beginning of said root canal a flat surface that surrounds and is transverse to the length of said root canal; (b) carrying out a radiograph of the tooth having placed a radiopaque element in contact with the reference surface; (c) measuring on said radiograph the position of a tooth apex with respect to the reference surface; (d) on the basis of said measurement, choosing an adaptor for the tool; (e) applying the adaptor to the tool; (f) introducing in the tooth the tool fitted with the adaptor and carrying out the reaming having as a limit the abutment of a surface of the adaptor against the tooth reference surface.

* * * * *